US009714448B2

(12) United States Patent  
Kubista et al.

(10) Patent No.: US 9,714,448 B2  
(45) Date of Patent: Jul. 25, 2017

(54) LYSIS AND REVERSE TRANSCRIPTION FOR MRNA QUANTIFICATION

(71) Applicants: Michael Kubista, Moelndal (SE); Linda Stroembom, Goeteborg (SE); Neven Zoric, Goeteborg (SE)

(72) Inventors: Michael Kubista, Moelndal (SE); Linda Stroembom, Goeteborg (SE); Neven Zoric, Goeteborg (SE)

(73) Assignee: Roche Molecular Systems, Inc., Pleasanton, CA (US)

(*) Notice: Subject to any disclaimer, the term of this patent is extended or adjusted under 35 U.S.C. 154(b) by 409 days.

(21) Appl. No.: 14/097,694

(22) Filed: Dec. 5, 2013

(65) Prior Publication Data

US 2014/0212958 A1 Jul. 31, 2014

Related U.S. Application Data

(60) Division of application No. 13/008,949, filed on Jan. 19, 2011, now Pat. No. 8,623,602, which is a continuation of application No. PCT/EP2009/005516, filed on Jul. 30, 2009.

(30) Foreign Application Priority Data

Aug. 1, 2008 (EP) .................................. 08013816

(51) Int. Cl.
    *C12P 19/34* (2006.01)
    *C12Q 1/68* (2006.01)

(52) U.S. Cl.
    CPC .................................. *C12Q 1/686* (2013.01)

(58) Field of Classification Search
    USPC .............................. 435/6.12, 91.2, 91.1, 810
    See application file for complete search history.

(56) References Cited

U.S. PATENT DOCUMENTS

| | | | |
|---|---|---|---|
| 5,118,801 A | 6/1992 | Lizardi et al. | |
| 5,210,015 A | 5/1993 | Gelfand et al. | |
| 5,487,972 A | 1/1996 | Gelfand et al. | |
| 5,538,848 A | 7/1996 | Livak et al. | |
| 5,804,375 A | 9/1998 | Gelfand et al. | |
| 6,174,670 B1 | 1/2001 | Wittwer et al. | |
| 6,541,204 B2 * | 4/2003 | Nilsen et al. | 435/6.1 |
| 7,491,495 B2 * | 2/2009 | Zielenski | C07H 21/02 435/6.11 |
| 8,309,303 B2 * | 11/2012 | Korfhage | C12Q 1/6806 435/6.1 |
| 2002/0009794 A1 | 1/2002 | Danenberg et al. | |
| 2006/0286557 A1 * | 12/2006 | Basehore et al. | 435/6 |

FOREIGN PATENT DOCUMENTS

| | | |
|---|---|---|
| CA | 2526409 | 12/2004 |
| EP | 1529841 A1 | 5/2005 |
| EP | 0389063 B2 | 10/2006 |
| WO | 9639536 A1 | 12/1996 |
| WO | 9746707 A3 | 12/1997 |
| WO | 9746712 A3 | 12/1997 |
| WO | 9746714 A1 | 12/1997 |
| WO | 03064605 A3 | 8/2003 |
| WO | 2005090984 A1 | 9/2005 |
| WO | 2005116245 A3 | 12/2005 |
| WO | WO 2006/103039 A1 * | 10/2006 |
| WO | 2008135197 A1 | 11/2008 |

OTHER PUBLICATIONS

Taube et al. (Eur. J. Biochem., 1998, vol. 258, p. 1032-1039).*
Ambroise-Thomas et al. Transactions of the Royal Society of Tropical Medicine and Hygiene, 1988, vol. 82, p. 360-362.*
Chin et al., "Lab-on-a-chip devices for global health: Past studies and future opportunities," Lab Chip, 2007, vol. 7, pp. 41-57.*
International Search Report issued Sep. 29, 2009 in PCT Application No. PCT/EP2009/005516.
International Preliminary Report on Patentability issued May 27, 2010 in PCT Application No. PCT/EP2009/005516.
Bengtsson, Martin et al., Quantification of mRNA in single cells and modelling of RT-qPCR induced noise, BMC Molecular Biology, Jul. 17, 2008, pp. 63-73, vol. 9, No. 1.
Boom, R. et al., Rapid and Simple Method for Purification of Nucleic Acids, Journal of Clinical Microbiology, Mar. 1990, pp. 495-503, vol. 28, No. 3.
Freeman, Willard M. et al., Quantitative RT-PCR: Pitfalls and Potential, BioTechniques, Jan. 1999, pp. 112-125, vol. 26, No. 1.
Hartshorn, Cristina et al., Rapid, single-tube method for quantitative preparation and analysis of RNA and DNA in samples as small as one cell, BMC Biotechnology, 2005, 5:2, Jan. 13, 2005, pp. 1-13.
Kawasaki, Ernest S., Microarrays and the Gene Expression Profile of a Single Cell, Annals of the New York Academy of Sciences, 2004, pp. 92-100, vol. 1020.
Matthews, Jayne A. and Kricka, Larry J., Analytical Strategies for the Use of DNA Probes, Analytical Biochemistry, 1988, pp. 1-25, vol. 169.
Sagner, Gregor and Goldstein, Cornelia, Principles, Workflows and Advantages of the New LightCycler Relative Quantification Software, Biochemica, 2001, pp. 15-17, vol. 3.
Yamada, Osamu et al., A new method for extracting DNA or RNA for polymerase chain reaction, Journal of Virological Methods, 1990, pp. 203-210, vol. 27, No. 2.
Yamaguchi, Masahiko et al., Effect of Different Laboratory Techniques for Guanidinium-Phenol-Chloroform RNA Extraction on A260/A280 and on Accuracy of mRNA Quantitation by Reverse Transcriptase-PCR, PCR Methods and Applications, May 1992, pp. 286-290, vol. 1, No. 4.

* cited by examiner

*Primary Examiner* — Young J Kim
(74) *Attorney, Agent, or Firm* — Dinsmore & Shohl LLP

(57) ABSTRACT

The present invention is directed to a method for performing an RT-PCR for amplifying a target RNA including the steps of (i) cultivation of a population of adherent cells in a cell culture vessel (ii) lysis of the population of adherent cells which is supposed to contain the target RNA in the sample vessel with a lysis buffer comprising between 0.05 M and 1 M of a chaotropic agent (iii) adding reagents to the sample vessel which are necessary to perform a reverse transcription reaction such that the chaotropic agent is present in a concentration of about 10 to 60 mM in the sample vessel, and reverse transcribing the target RNA and (iv) amplifying the first strand cDNA by means of subjecting the sample to multiple cycles of a thermocycling protocol.

12 Claims, 4 Drawing Sheets

LYSIS AND REVERSE TRANSCRIPTION FOR MRNA QUANTIFICATION

RELATED APPLICATIONS

This application is filed as a division of U.S. application Ser. No. 13/008,949, filed Jan. 19, 2011, which was filed as a continuation of PCT/EP2009/005516, filed Jul. 30, 2009, and which claims priority to EP 08013816.7, filed Aug. 1, 2008.

FIELD OF THE INVENTION

The present invention provides a new method for gene expression monitoring by means of performing RT-PCR. More precisely, the present invention discloses a possibility to lyse adherent cells in the vial in which they have been cultivated and subsequently, reverse transcribe the RNA contained in the lysate into single stranded cDNA in the same vial.

BACKGROUND OF THE INVENTION

Cells in a population are in many aspects unique in their characteristics, even in a seemingly homogenous culture or tissue. Gene expression levels show large cell to cell variations, due to external (extrinsic) and internal (intrinsic) sources of factors Likewise, when exposed to identical stimuli, cells often behave stochastically. This means that data obtained from a population of cells cannot be assumed to reflect the behavior of the individual cell. It has been suggested that cells can respond to stimuli by bursts in transcriptional activity and operate as a binary switch; that is in an all-or-none fashion.

Usually, gene expression on the RNA level is monitored on a routine basis by a multi-step procedure. First, the respective cellular sample is removed from the culture vessel. In case of adherent cells harvesting may be supported by trypsination (treatment with a Trypsin-EDTA solution) in order to detach the adherent cell from the solid support. Secondly, the collected cells are pelleted and subjected to cell lysis. As a third step it is usually required to at least partially purify the RNA or mRNA that is present in the sample (EP 0 389 063). Afterwards, a first strand cDNA synthesis step is performed with an RNA dependent DNA polymerase such as AMV (Roche Applied Science Cat. No: 11 495 062) or MMuLV (Roche 11 062 603) Reverse Transcriptase.

Subsequently, the amount of generated cDNA is quantified either by means of quantitative PCR (Sagner, G., and Goldstein, C., BIOCHEMICA 3 (2001) 15-17) or, alternatively by means of amplification and subsequent hybridization onto a DNA microarray (Kawasaki, E. S., Ann. N.Y. Acad. Sci. 1020 (2004) 92-100). In case of PCR, a one step RT-PCR may be performed, characterized in that the first strand cDNA synthesis and subsequent amplification are catalyzed by the same Polymerase such as T.th Polymerase (Roche Applied Science Cat. No. 11 480 014).

In traditional real time RT-PCR or qRT-PCR, RNA is first isolated from cells in a time consuming procedure that can lead to a loss of material. Using the CellsDirect cDNA Synthesis System (Invitrogen Cat No. 11737-030), the cells are lysed and the cDNA is generated from the lysate in a single tube with minimal handling and no sample loss. DNase I is added to eliminate genomic DNA prior to first-strand synthesis. After synthesis, the first-strand cDNA can be transferred directly to the qPCR reaction without intermediate organic extraction or ethanol precipitation. This kit has been optimized for small cell samples, ranging from 10,000 cells down to a single cell. A similar protocol is disclosed in (WO 08/135,197).

In this context, the technical problem underlying the present invention was to provide a high throughput method and a kit that allow for a further simplified gene expression monitoring analysis protocol.

SUMMARY OF THE INVENTION

Thus, the present invention is directed to a method for performing an RT-PCR for amplifying a target RNA comprising the steps of a) cultivation of a population of adherent cells in a cell culture vessel b) lysis of said population of adherent cells which is supposed to contain said target RNA in said sample vessel with a lysis buffer comprising between 0.05 M and 1 M of a chaotropic agent c) adding reagents to said sample vessel which are necessary to perform a reverse transcription reaction such that the said chaotropic agent is present in a concentration of about 10 to 60 mM in said sample vessel, and reverse transcribing said target RNA into first strand cDNA d) amplifying said first strand cDNA by means of performing multiple cycles of a thermocycling protocol.

In one major embodiment, the step of amplifying is monitored in real time.

Preferably, the chaotropic agent is Guanidine Thiocyanate.

Also preferably, the lysis buffer comprises between about 0.2 and 0.5 M of the chaotropic agent.

During step c) of the inventive method, the chaotropic agent is present in a concentration of about 30 to 50 mM and preferably about 40 mM.

Also preferably, step b) of the new method is performed in the presence of a non ionic detergent which for example may be NP40. During step c), said non ionic detergent has a V/V of 0.1 to 2%.

Also preferably, step a) comprises the addition of a carbohydrate, which may be a sugar or a dextran.

In a particular embodiment, a DNAse is added between steps b) and c) or during step c. Preferably, said DNAse is predominantly a double strand specific DNAse, and preferably DNAse I or Shrimp Nuclease.

In another particular embodiment, which is not mutually exclusive with the one disclosed above, Proteinase K is added either during step b) or prior to step c).

In a second aspect, the present invention also provides for a kit comprising a disposable for cultivating at least one cell sample, a lysis buffer, and a DNA polymerase comprising reverse transcriptase activity.

In addition, such a kit may further comprise at least one additional component selected from a group consisting of a non ionic detergent, a carbohydrate, a DNAse and a Protease.

BRIEF DESCRIPTION OF THE DRAWINGS

All figures comprise an upper panel representing a qPCR amplification curve and a lower panel representing a melting curve analysis. Amplification curves occurring on the more left side correspond to replicate measurements, whereas amplification curves on the more right side correspond to controls without addition of Transcriptor enzyme. Melting peaks on the right side correspond to specific amplification products of replicates, whereas melting peaks on the more left side correspond to primer dimer formation in controls without Transcriptor enzyme.

DETAILED DESCRIPTION OF THE INVENTION

Figure 1:
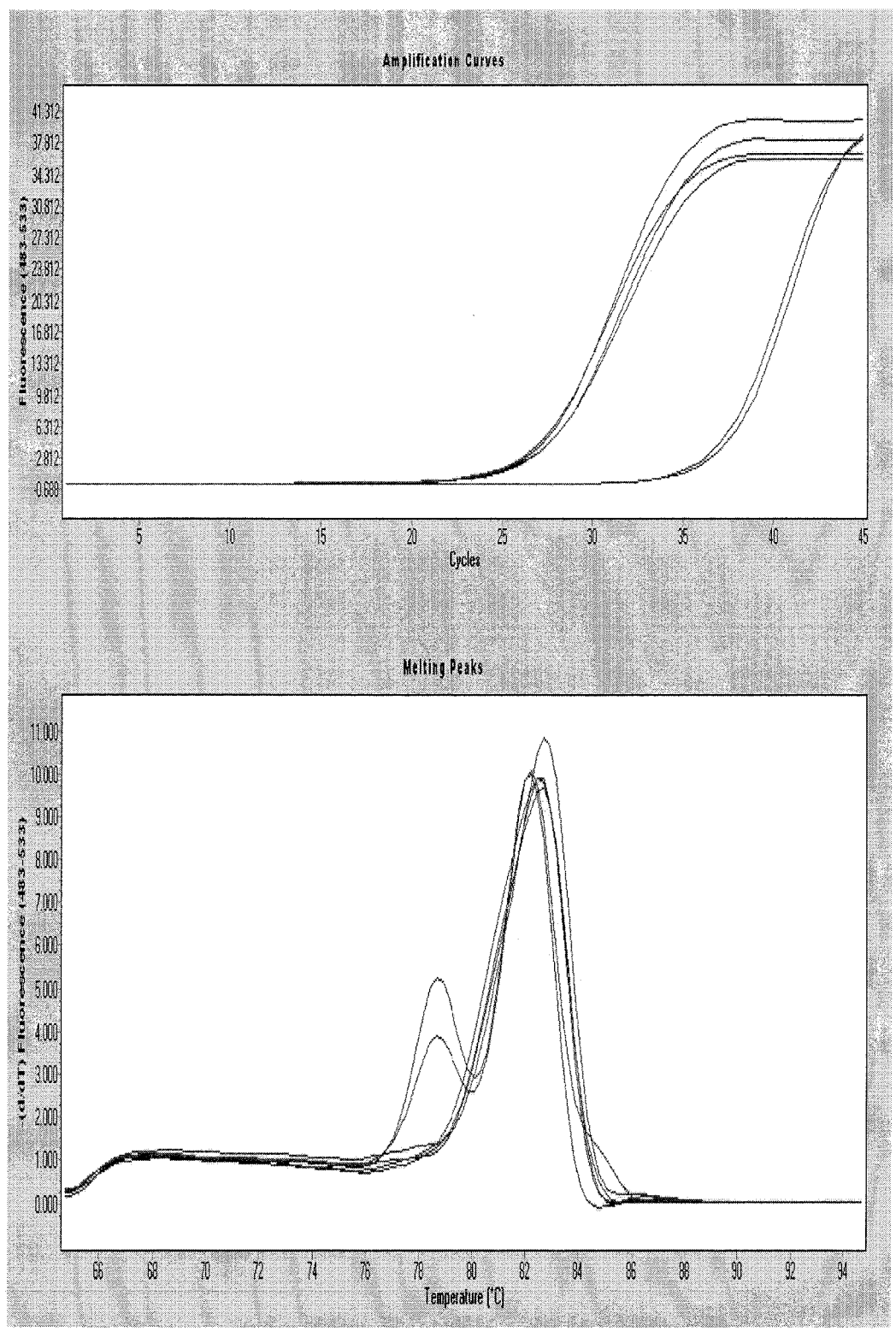
FIG. 1: qPCR and melting curve analysis of the ACTB expression in mouse astrocytes according to the present invention as embodied by example 1 (1:1 sample dilution)
Figure 2:
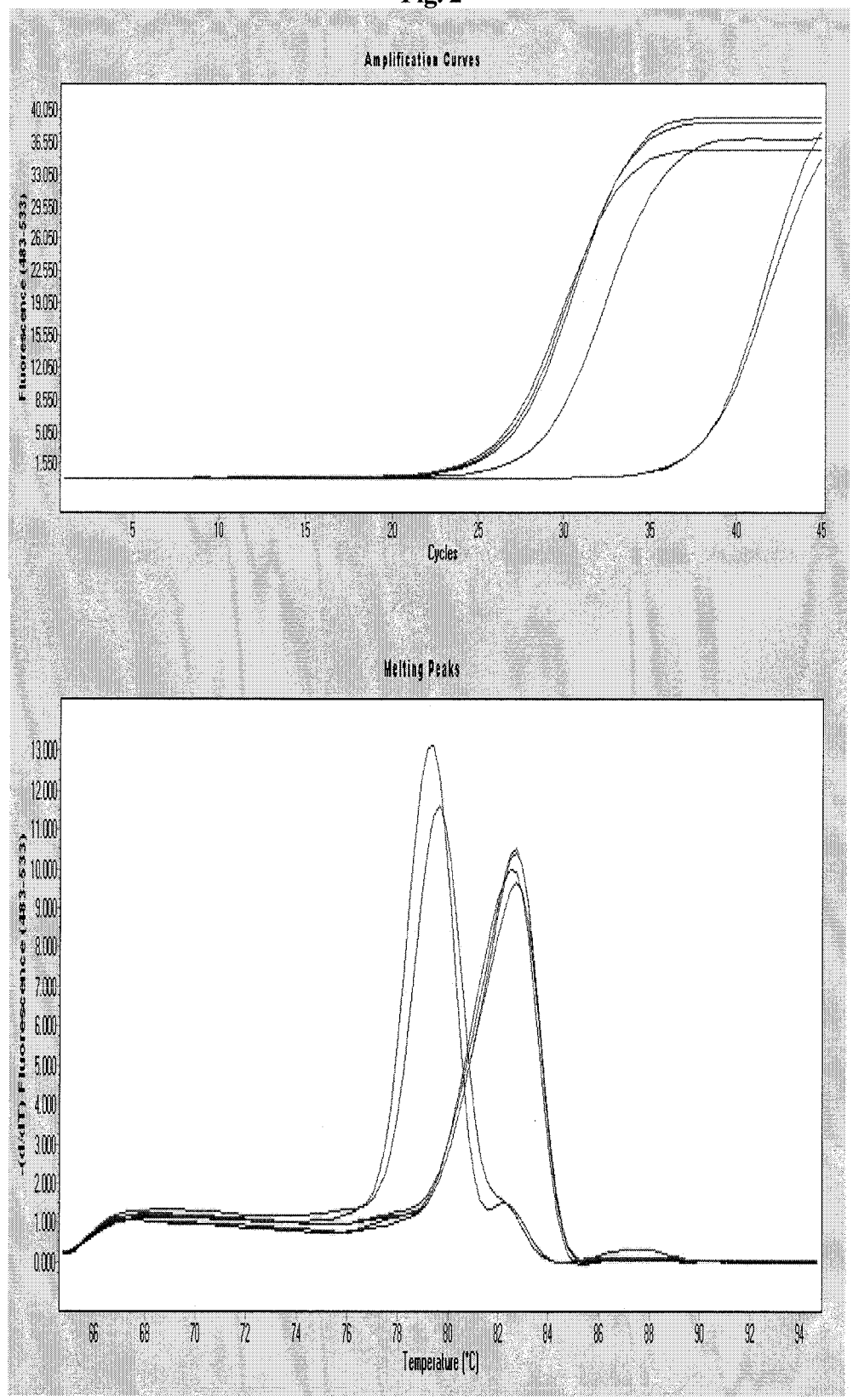
FIG. 2: qPCR and melting curve analysis of ACTB expression in mouse astrocytes according to the present invention as embodied by example 1 (1:4 sample dilution)

According to the present invention, it is possible to perform a lysis of adherent eukaryotic cells or even prokaryotic cells in a certain cultivation vessel and in the same cultivation vessel performing a Reverse Transcriptase reaction in order to generate single stranded cDNA.

Thus, the present invention more precisely is directed to a method for performing an RT-PCR for amplifying a target RNA comprising the steps of a) cultivation of a population of adherent cells in a cell culture vessel b) lysis of said population of adherent cells which is supposed to contain said target RNA in said sample vessel with a lysis buffer comprising between 0.05 M and 1 M of a chaotropic agent.

c) adding all reagents to said sample vessel which are necessary to perform a reverse transcription reaction such that the said chaotropic agent is present in a concentration of about 10 to 60 mM in said sample vessel, and reverse transcribing said target RNA into first strand cDNA d) amplifying said first strand cDNA by means of performing multiple cycles of thermocycling protocol.

Thus, cell cultivation, lysis, and the reverse transcription reaction, i.e. steps a) to c) are all performed in the same vessel. As a consequence and in contrast to most prior art methods, there is no purification of the lysate required prior to the performance of the reverse transcription reaction. In other words, step c) follows step b) without any intermediate purification step.

Step a), i.e. cultivation of a population of adherent cells in a cell culture vessel is defined as a step of growing a population of said adherent cells under appropriate cultivation conditions over a defined period of time such that the cells have a possibility to divide and the overall number of living cells increases at least by a factor of two.

Moreover, it is important to note that the protocols as used in the art require a trypsination step, which means that in order to detach the adherent cells from the solid support the cell culture is incubated with an appropriate buffer solution containing Trypsin-EDTA which are commercially available (e.g. Invitrogen Cat. No: 25200 056, Genaxxon Cat. No: 4260.0500). In contrast, the present invention does not require detachment of the cells from the solid support by trypsin, because the cells are directly lysed in situ.

Amplification according to step d) is usually performed in the form of a PCR reaction using a specific pair of amplification primers, which is designed to allow for the detection of a specific cDNA species.

The method according to the present invention may be used for a variety of different qualitative and quantitative applications. In principle, any type of RNA may be transcribed and amplified. Most importantly, the method according to the present invention is applicable for amplifying and detecting mRNAs in a qualitative and quantitative manner. Thus, the present invention is particularly applicable for monitoring gene expression.

In order to control the process of harvesting, cell lysis and reverse transcription, the samples may be spiked with a control RNA. The control RNA preferably is an artificial RNA, which during the step of reverse transcription is transcribed into a cDNA that can be discriminated from the RNA of the sample. In case of using specific primers for the reverse transcription step, the artificial RNA may be derived from in vitro transcription of a genetically engineered DNA template that either comprises an insertion or only partially represents the target sequence which shall become analyzed.

The biological sample preferably consists of adherent eukaryotic cells, i.e. the cells are cultivated and grow by being attached to a solid support that is part of a cultivation vessel. For the inventive method, any type of cultivation vessel can be used. Examples, which however, are not limiting, the scope of the present invention are Petri dishes and cultivation bottles having an inner surface that is suited to be a solid support for the growth of adherent cells. These types of cultivation bottles allow for preparation of a specific type of cDNA in large quantities.

Other examples are microtiter plates in the 6-well, 24-well, 96-well, 384-well, or 1536-well format as they are commonly used in the art. In case the method according to the present invention is performed in such microtiter plates, it is possible to cultivate, lyse and reverse transcribe multiple samples in parallel. More precisely, cell cultivation, cell lysis, dilution, any addition of additives and the reverse transcriptase reaction are carried out in the same reaction vessel. Therefore, the inventive method is particularly useful for high throughput analyses of multiple samples of adherent cells within an automated process. If the reaction vessels are arranged together in the form of a 24, 96, 384 or 1536 well microtiter plate according to standards that are established in the art, the lysis reagent, the various additives and the reagents necessary for performing a Reverse Transcriptase reaction can be added to the samples by liquid handling robotic instruments.

Thus, in a particular aspect, the present invention is directed to a method for performing multiple RT-PCR reactions for amplifying at least one target RNA in parallel, comprising the steps of:

a) cultivation of multiple populations of adherent cells in separate wells of a microtiter plate b) lysis of said multiple populations of adherent cells which are supposed to contain said target RNA in said wells of said microtiter plate with a lysis buffer comprising between 0.05 M and 1 M of a chaotropic agent in order to generate multiple samples c) adding all reagents to each of said multiple samples in said wells which are necessary to perform a reverse transcription reaction such that the said chaotropic agent is present in a concentration of about 10 to 60 mM in said wells of said microtiter plate, and reverse transcribing said target RNA present in each sample into first strand cDNA, d) amplifying said first strand cDNA contained in each sample by means of performing multiple cycles of a thermocycling protocol.

Within the scope of the invention, preferably 6, 24, 96, 384 or even 1536 populations can be processed in parallel. Again, amplification according to step d) is usually performed in the form of a PCR reaction using a specific pair of amplification primers, which is designed to allow for the detection of a specific cDNA species. In one embodiment, the plurality of multiple wells may contain different cell populations, originating from different cell lines, or identical cell lines, which have been pre-treated under different conditions. In this case, the multiple PCR amplifications are performed using the same pair of amplification primers in order to study the expression of a specific gene under different conditions.

Alternatively, the majority of wells may comprise the same type of cell population originating from the same origin. In this case, multiple different pairs of amplification primers may be chosen in order to study the expression of many different genes in parallel. However, a person skilled in the art will understand that both approaches as disclosed are not mutually exclusive and, depending on the scientific question to be analyzed, will be able to design an assay setup with an appropriate number of different cell types and an appropriate number of different PCR primer pairs in order to achieve an optimal use of the complete number of wells that are present in the respective microtiter plate.

In addition, the potential of such a parallel analysis can even be improved by means of multiplex PCR, characterized in that multiple primer pairs for the amplification of different species of cDNA are used for the same sample. In particular, such a setup is advantageous for relative RT-PCR quantification experiments, characterized in that the expression of a certain gene is monitored relatively to the expression of a so called housekeeping gene, which is constitutively expressed at equal levels. Prominent examples of such housekeeping genes are the PBDG, GAPDH, and ACTB as well as 18 S and 26 S RNA genes.

According to the present invention, lysis of the adherent cells is achieved by means of directly adding a lysis buffer, while the cells are still attached to a solid support surface. This is only possible if the lysis buffer comprises a chaotropic reagent. According to common understanding in the art, a chaotropic reagent is a substance which disrupts the three dimensional structure in macromolecules such as proteins, DNA, or RNA and denatures them. Chaotropic agents interfere with stabilizing intramolecular interactions mediated by non-covalent forces such as hydrogen bonds, Van der Waals forces, and hydrophobic effects. Chaotropic reagents include but are not limited to urea, some lithium salts such as lithium perchlorate and guanidinium salts such as guanidinium chloride. In the context of the present invention, the particularly preferred agent is guanidine thiocyanate.

In order to enable the possibility to perform the reverse transcriptase reaction directly within the lysate without any intermediate purification step, it is required to use only limited amounts of said chaotropic agent for lysis of the cell sample, such that during step b), the activity of reverse transcriptase is not appreciably affected. Therefore, the lysis buffer added in step b) comprises preferably between about 0.2 and 0.5 M of the chaotropic agent. Furthermore, after addition of additional reagents at the beginning of step c) the chaotropic agent is present in a concentration of about 30 to 50 mM and preferably about 40 mM.

In one embodiment, step b) of the present invention is performed in the presence of a non ionic detergent such as NP40. Alternatively, step b) comprises the addition of a PCR compatible humectant, which results in an effective avoidance of evaporation effects, if samples with only small volumes need to be processed. Preferably, a carbohydrate such as a sugar or a dextran may be used as a humectants in the context of the present invention. If NP40 or another non ionic detergent is added, then the amount of detergent should be chosen in such a way that during step c) said detergent is present in a V/V amount of 0.1 to 2%.

Cell harvesting and lysis according to the present invention may be performed at various temperatures. Step b) of the inventive method is usually performed for at least 5 minutes i.e. between 16° C. and 24° C. The maximum time which is required for lysis under these circumstances is about 30 minutes. Similarly, step b) can be performed for at least 10 minutes even below ambient temperature, but above 5° C. The maximum time which is required for lysis under these circumstances is about 60 minutes. These conditions are very favorable for the avoidance of any evaporation effects, if samples with small volumes are processed. It also eliminates the need for heating.

Yet, in order to accelerate and improve lysis of the cultivated adherent cells, the lysis buffer may be supplemented with Proteinase K. In this case, step b) is performed for at least 5 minutes at a temperature between about 55° C. to 85° C. in the presence of Proteinase K in concentrations of about 0.05 to 5 mg/ml and preferably 0.1-1 mg/ml. Optionally, said Proteinase K may be irreversibly inactivated by means of subsequent incubation either between step b) and step c) or between step c) and step d) for at least 5 minutes but usually not more than 30 minutes at a temperature between about 80° C. to 90° C.

As according to the present invention, cell lysis and reverse transcription are performed in the same reaction vessel, it has been proven to be highly advantageous if the genomic DNA that is contained in the lysed cells can selectively be removed, while the cellular RNA is maintained intact. The most effective possibility to achieve this effect is an enzymatic removal by means of including a DNAse digestion step. Thus, in one major embodiment of the present invention, step b) is performed in the presence of a double strand specific DNAse. Preferably, such a DNAse is an exclusively double strand specific DNAs such as DNAse I (Roche Applied Science Cat. No. 04 716 728) or Shrimp DNAse (U.S. Pat. No. 6,541,204) at a concentration of about 0.1 Unit per 50 l reaction (USB, Cat. No: 73814). However, since during step d) the single stranded cDNA is further subjected to a DNA Polymerase catalyzed amplification reaction such as a PCR reaction, it is highly advantageous to inactivate said DNAse prior to the amplification reaction. Thus, for inactivation of DNAse activity, in a specific embodiment the sample is incubated for at least 5 minutes but not longer than 60 minutes between step b) and step c) or step c) and step d) at a temperature between about 80° C. to 90° C. Alternatively, if the DNAse is Shrimp DNAse, the denaturation during the first cycle of the PCR reaction in step d) is usually sufficient.

For the first strand cDNA synthesis, primers with an antisense sequence are used. These primers are either specific primers, olig-dT primers, which bind to the poly-A-tail of an mRNA, or random primers such as random hexamer primers. For subsequent PCR, a sequence specific primer in sense orientation is used as a forward primer. The reverse primer is a specific primer which may be identical to the specific primer used in the first strand cDNA synthesis reaction. Alternatively, the reverse primer, which hybridizes to a sequence located upstream from the binding side of the primer that has been used for the reverse transcriptase reaction.

The present invention is applicable for performing one step RT-PCR of sequences of practicably any amplicon size up to 5 kb.

The present invention is particularly useful for performing 2-step RT PCR, i.e. in a first reaction, the RNA is reverse transcribed into single stranded cDNA. Examples for RNA dependent DNA polymerases that can be used for this step are AMV Reverse Transcriptase (Roche Applied Science Cat. No. 11 495 062), MMuL V Reverse Transcriptase (Roche Applied Science Cat. No. 03 531 317). Subsequently, all reagents are added that are required to amplify the generated single stranded cDNA by means of PCR, such as a thermostable DNA dependent DNA polymerases as well as target specific forward and reverse amplification primers.

The inventive method can also be used for performing 1-step PCR, characterized in that all reagents and enzymes necessary for RT-PCR are added in step c) prior to the reverse transcription. For example, the DNA polymerase of Carboxydothermus hydrogenoformans is capable of performing a 1-step PCR (Roche Applied science Catalog No. 12016338001). Alternatively, the one step RT-PCR method according to the present invention is performed using an enzyme mixture comprising a DNA-template dependent thermostable DNA Polymerase capable of performing a PCR reaction and an RNA-template dependent DNA Polymerase capable of performing the reverse transcriptase step of the one step RT-PCR reaction such as AMV Reverse Transcriptase.

Usually, however, the material of the majority of cell culture vessels used for cultivating adherent cells will not be thermostable, and the respective vials will not fit into a thermocycling instrument. Thus, for a 1-step RT-PCR protocol, after the step of reverse transcription, the samples of the generated first strand cDNA are transferred from the cultivation vessels into reaction vessels that can be used in conjunction with a thermocycler instrument without an intermediate addition of further reagents. Yet, if the material of the cell culture vessels used for cultivating said adherent cells is thermostable, then step d) may also be performed in said vessels. In particular, if the cell culture vessels are arranged in a microtiter plate format, then said microtiter plate can be transferred directly to thermocycler instruments that are configured to take up such plates.

In one major embodiment, the step of amplifying is monitored in real time. Such a monitoring in real time is characterized in that the progress of said one-step RT-PCR reaction is monitored in real time. Different detection formats are known in the art. The below mentioned detection formats have been proven to be useful for RT-PCR and thus provide an easy and straight forward possibility for gene expression analysis:

a) Taqman Hydrolysis Probe Format:

A single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured. TaqMan probe assays are disclosed in detail in U.S. Pat. Nos. 5,210,015, 5,538,848, and 5,487,972. TaqMan hybridization probes and reagent mixtures are disclosed in U.S. Pat. No. 5,804,375.

b) Molecular Beacons:

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

c) FRET Hybridization Probes:

The FRET Hybridization Probe test format is especially useful for all kinds of homogenous hybridization assays (Matthews, J. A., and Kricka, L. J., Analytical Biochemistry 169 (1988) 1-25). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET component as a quantitative measurement of hybridization event.

In particular, the FRET Hybridization Probe format may be used in real time PCR, in order to detect the amplified target DNA. Among all detection formats known in the art of real time PCR, the FRET-Hybridization Probe format has been proven to be highly sensitive, exact and reliable (WO 97/46707; WO 97/46712; WO 97/46714). As an alternative to the usage of two FRET hybridization probes, it is also possible to use a fluorescent-labeled primer and only one labeled oligonucleotide probe (Bernard, P. S., et al., Analytical Biochemistry 255 (1998) 101-107). In this regard, it may be chosen arbitrarily, whether the primer is labeled with the FRET donor or the FRET acceptor compound.

d) SybrGreen Format

It is also within the scope of the invention, if real time PCR is performed in the presence of an additive according to the invention in case the amplification product is detected using a double stranded nucleic acid binding moiety. For example, the respective amplification product can also be detected according to the invention by a fluorescent DNA binding dye which emits a corresponding fluorescence signal upon interaction with the double-stranded nucleic acid after excitation with light of a suitable wavelength. The dyes SybrGreenI and SybrGold (Molecular Probes) have proven to be particularly suitable for this application. Intercalating dyes can alternatively be used. However, for this format, in order to discriminate the different amplification products, it is necessary to perform a respective melting curve analysis (U.S. Pat. No. 6,174,670).

Kits According to the Present Invention

In another aspect, the present invention also provides for a kit comprising (i) a disposable for cultivating at least one cell sample,
(ii) a lysis buffer, and (iii) a DNA polymerase comprising reverse transcriptase activity (Reverse Transcriptase)

The disposable (i) may be any kind of disposable that is suited for the cultivation of at least one cell population. Preferably, such a disposable is a microtiter plate with preferably 6-, 24-, 96-, 384-, or 1536 wells. In a specific embodiment, such a disposable is thermostable and compatible with a thermocycler instrument.

The lysis buffer (ii) is a buffer comprising between 0.05 M and 1 M of a chaotropic agent. The agent itself is preferably guanidine thiocyanate. Optionally, the kit may contain Proteinase K within the lysis buffer in a concentration of about 0.05 to 5 mg/ml and preferably 0.1-1 mg/ml, or as a standalone reagent with an at least 5 fold higher stock concentration. Also optionally, the kit may contain a dextran or a non ionic detergent, which is preferably NP, either within the lysis buffer in a V/V amount of 0.1 to 2%, or alternatively in a separate vial an at least 5 fold higher stock concentration. Also optionally, the kit may contain a predominantly double strand specific DNAse such as DNAse I or Shrimp Nuclease in a separate vial at a concentration of at least 0.02 unit.

The Reverse Transcriptase (iii) is either an exclusively RNA dependent DNA polymerase that such as AMV Reverse Transcriptase (Roche Applied Science Cat. No. 11 495 062), MMuLV Reverse Transcriptase (Roche Applied Science Cat. No. 011 062 603), and the recombinant Transcriptor Reverse Transcriptase (Roche Applied Science Cat. No. 03 531 317). Component (iii) may also be a 1-step RT PCR enzyme such as the DNA polymerase of Carboxydothermus hydrogenoformans, or a mixture of a Reverse Transcriptase enzyme and a thermostable DNA dependent DNA polymerase.

A kit according to the present invention may contain a buffer, deoxynucleoside triphosphates that are required for a first strand cDNA synthesis, as well as respective primers such as an olig-dT primer, a random hexamer primer or even a specific primer. Together with the polymerase, one, several or all of these reagents may be combined into one vial as a respective master mix.

Furthermore, such a kit according to the present invention may comprise a thermostable DNA polymerase such as Taq Polymerase, and all other reagents necessary for performing the amplification reaction, including but not limited to a buffer reagent, additional deoxynucleoside triphosphates, and sequence specific amplification primers. In addition, the kit may comprise reagents necessary for detection of the amplicon during qPCR such as at least one fluorescently labeled hybridization probe, or a double stranded fluorescent dye.

EXAMPLE 1

Mouse astrocyte cells were seeded at two different concentrations (1:1, 1:4) intoa 384-well cell culture plate with approximately 1000 or 250 cells per vial and allowed to grow. After about 96h, the culture media was removed and the cells were washed with cold PBS. 2 µl of lysis buffer was added and the cells were incubated for 10 minutes at room temperature. Composition of lysis buffer was as follows:
   0.2 M guanidine thiocyanate
   10 mg/µl polyinosinic acid Transcriptor Rt reagents (Roche Applied Science Cat. No. 03 531 317) were added to a final RT volume of 20 µl. In No RT controls, the reverse transcriptase was omitted from the RT mix. The cell culture plate containing the RT reactions was incubated according to the following thermocycling protocol:
   25° C. for 10 minutes
   55° C. for 30 minutes
   85° C. at 5 minutes
   Chill on ice.

Subsequently, the cDNA was diluted to 50 µl in nuclease free water. 2 µl of cDNA was analyzed in a 10 µl PCR using the LightCycler 480 SYBR Green I Master pre-mix (Roche Applied Science Cat. No. 04 707 516) and primers suitable for amplifying ACTB and 18S rRNA (TATAA Biocenter, endogenous control gene panel). The expression of the ACTB and 18S rRNA genes was quantified on a LightCycler 480 real-time PCR instrument (Roche Applied Science Cat. No. 05 015 278) and Ct-values were determined according to the manufacturer's instructions. Low Ct values correspond to a high degree of expression.

TABLE 1

Ct values obtained for the 1:1 dilution

| Sample name | ACTB - Ct | 18S rRNA - Ct |
| --- | --- | --- |
| Well 1 | 27.62 | 11.52 |
| Well 2 | 27.23 | 11.49 |
| Well 3 | 27.9 | 12.06 |
| Well 4 | 27.8 | 11.81 |
| NoRT 1 | 36.95 | 32.56 |
| NoRT 2 | 37.35 | 30.45 |

TABLE 2

Ct values obtained for the 1:4 dilution

| Sample name | ACTB - Ct | 18S rRNA - Ct |
| --- | --- | --- |
| Well 1 | 26.82 | 10.56 |
| Well 2 | 27.06 | 10.52 |
| Well 3 | 28.85 | 11.7 |
| Well 4 | 26.47 | 10.06 |
| NoRT 1 | 38.28 | 32.29 |
| NoRT 2 | 38.18 | 32.5 |

As can be deduced from the tables, the Ct values obtained for respective quadruplicates are highly reproducible, indicating the high performance quality of the claimed invention.

In addition, results of qPCR and subsequent melting curve analysis for the ACTB gene are shown in FIGS. 1 (1:1) and 2 (1:4).

EXAMPLE 2

Mouse astrocyte cells were seeded into a 384-well cell culture plate with an average number of approximately 125 cells per vial and allowed to grow. After about 96h, the culture media was removed and the cells were washed with cold PBS buffer. The PBS buffer was then replaced with RNA later (Ambion, Cat. No. 7020), and the cells were stored in the fridge for 11 days. The RNA later was then removed, and the cells were washed once or twice with cold PBS. 4 µl of lysis buffer containing 0.2 M guanidine thiocyanate and 5 ml/µl polyinosinic acid was added and the cells were incubated for 10 minutes at room temperature. Transcriptor RT reagents were added to a final RT volume of 20 µl. In No RT controls the reverse transcriptase was omitted from the RT mix. The cell culture plate containing the RT reactions was incubated according to the following protocol:

25° C. for 10 minutes
50° C. for 30 minutes
85° C. at 5 minutes
Chill on ice

The cDNA was diluted to 50 µl in nuclease free water. Analogous to example 1, 2 µl of cDNA was analyzed in a 10 µl PCR using the LightCycler 480 SYBR Green I Master pre-mix. Real-time PCR measuring the 18S rRNA, ACTB, GAPDH and TUBBS genes with appropriate primers (TATAA Biocenter, endogenous control gene panel) was performed on a LightCycler 480 real-time PCR instrument. Results of Ct values obtained are shown in table 3.

TABLE 3

| Sample name | ACTB - Ct | 18S rRNA - Ct | GAPDH - Ct | TUBB5 - Ct |
|---|---|---|---|---|
| 1 PBS wash well 1 | 26.14 | 10.95 | 24.05 | 23.96 |
| 1 PBS wash well 2 | 26.20 | 10.55 | 23.89 | 23.85 |
| 1 PBS wash well 3 | 26.63 | 10.80 | 24.00 | 24.03 |
| 1 PBS wash NoRT | 32.06 | 28.19 | 28.74 | 40.00 |
| 2 PBS washes well 1 | 27.67 | 11.58 | 24.65 | 25.32 |
| 2 PBS washes well 2 | 27.17 | 11.31 | 24.51 | 25.20 |
| 2 PBS washes well 3 | 27.13 | 11.34 | 24.48 | 25.17 |
| 2 PBS washes NoRT | 36.47 | 30.69 | 32.94 | N/A |

Figure 3:
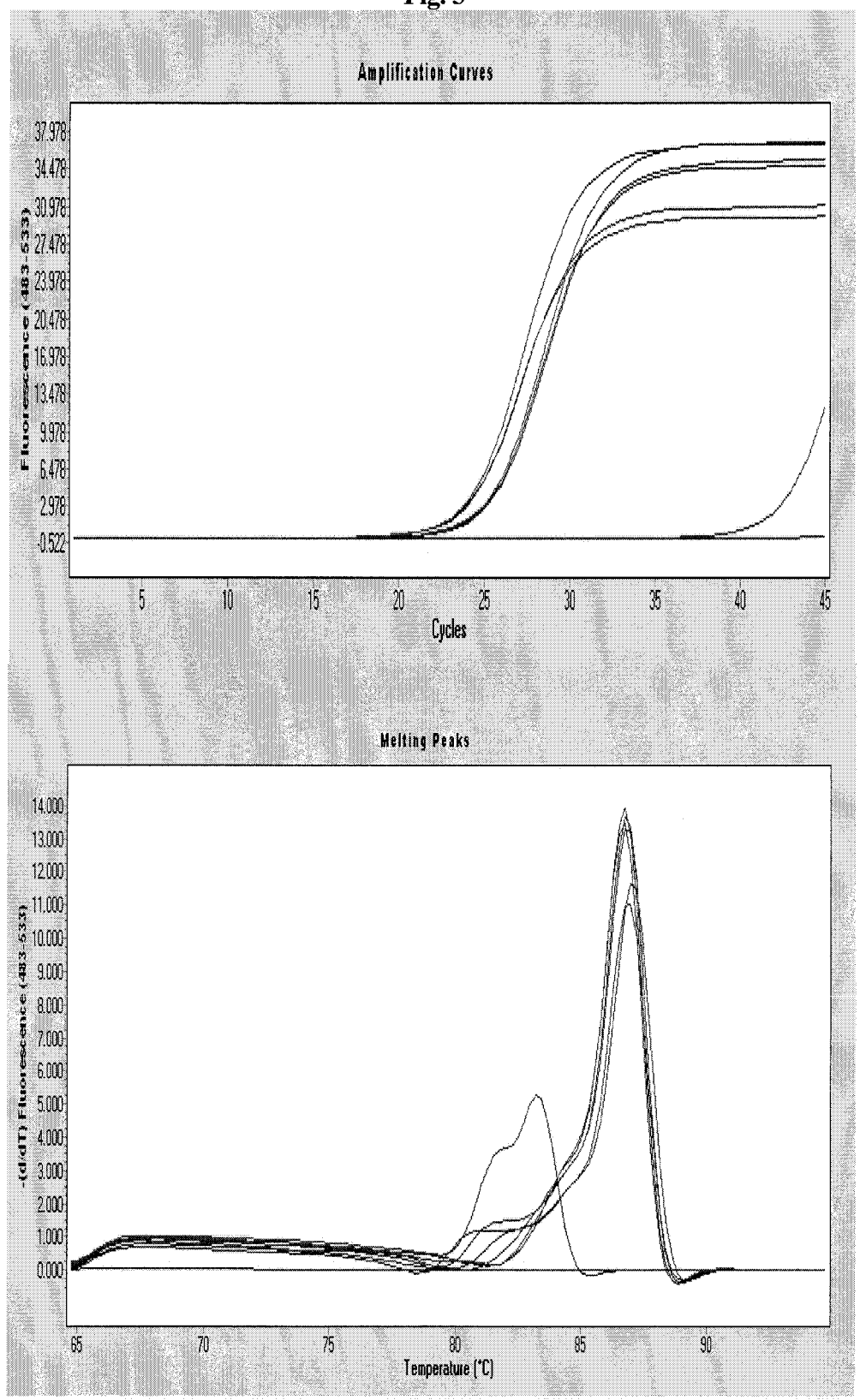
FIG. 3: qPCR and melting curve analysis of TUBBS expression in mouse astrocytes according to the present invention as embodied by example 1 (1:1 dilution)

Again, the very similar Ct values obtained for the triplicates show the superior performance of the inventive method irrespective of the gene that is analyzed. Performance is also demonstrated in FIG. 3, which shows the amplification and melting curves obtained for the TUBBS gene.

EXAMPLE 3

Human cultured HeLa cells were seeded into a 96-well cell culture plate with an approximate number of 4000 cells per vial and allowed to grow. After about 48h, the culture media was removed and replaced with RNA later, and the cells were stored in the fridge for 24 h. The RNA later was then removed, and the cells were washed with cold PBS. 12.5 µl of lysis buffer according to example 1 was added and the cells were incubated for 10 minutes at room temperature. Transcriptor RT reagents were added to a final RT volume of 50 µl. In No RT controls the reverse transcriptase was omitted from the RT mix. The cell culture plate containing the RT reactions was incubated according to the following protocol:

25° C. for 10 minutes
50° C. for 30 minutes
85° C. at 5 minutes
Chill on ice

Analogous to example 1, 2 µl of cDNA was analyzed in a 10 µl PCR reaction using the LightCycler 480 SYBR Green I Master pre-mix. Real-time PCR measuring the ACTB, GAPDH, RPLP0 and HPRT1 genes with appropriate primers (TATAA Biocenter, endogenous control gene panel) was performed on a LightCycler 480 real-time PCR instrument. The Ct values obtained are shown in table 4.

TABLE 4

| Sample name | ACTB - Ct | GAPDH - Ct | RPLP0 - Ct | HPRT1 - Ct |
|---|---|---|---|---|
| Well 1 | 21.0 | 19.83 | 21.71 | 24.74 |
| Well 2 | 21.71 | 21.63 | 23.57 | 26.09 |
| Well 3 | 21.19 | 20.95 | 22.86 | 25.88 |
| Well 4 | 21.8 | 20.94 | 23.2 | 25.7 |
| Well 5 | 23.03 | 22.0 | 24.49 | 26.7 |
| NoRT | 40.0 | N/A | 40.0 | N/A |

Figure 4:
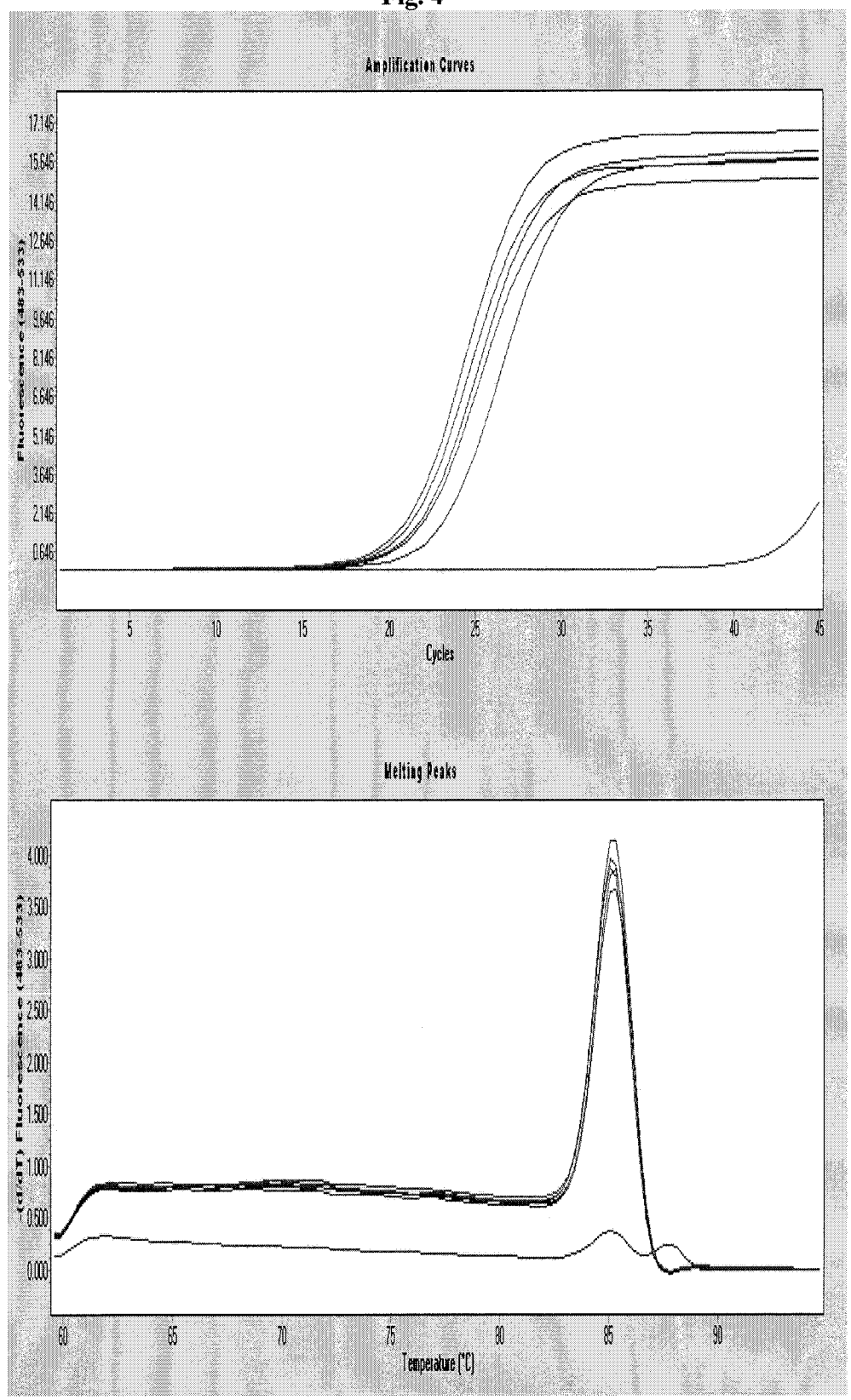
FIG. 4: qPCR and melting curve analysis of ACTB expression in HeLA cells according to the preset invention as embodied by example 1 (1:1 dilution)

The very similar Ct values obtained for the pentaplicates show the superior performance of the invented method irrespective of the cell type analyzed. Performance is also demonstrated in FIG. 4, which shows the amplification and melting curves obtained for the ACTB gene.

What is claimed:

1. A kit comprising:
   a disposable vessel suitable for cultivating at least one adherent cell sample; and
   a first volume of reagents comprising lysis buffer, an amount of a chaotropic agent in a concentration of between 0.05 M and 1M, and an amount of non-ionic detergent; and
   a second volume of reagents comprising reagents necessary to perform a reverse-transcription reaction, said reagents comprising a DNA polymerase capable of reverse transcriptase activity, wherein the first volume and the second volume added together equal a total reagent volume, said total reagent volume comprising the chaotropic agent in a concentration of between 10 and 60 mM.

2. The kit according to claim 1, wherein the first volume of reagents further comprises at least one additional reagent selected from the group consisting of a carbohydrate and a protease.

3. The kit according to claim 2, wherein the at least one additional reagent comprises carbohydrate.

4. The kit according to claim 2, wherein the at least one additional reagent comprises protease.

5. The kit according to claim 4, wherein the protease comprises proteinase K.

6. The kit according to claim 1, wherein the chaotropic agent is guanidine thiocyanate.

7. The kit according to claim 1, wherein the first volume comprises an amount of non-ionic detergent calculated to yield a concentration of between about 0.1% and about 2% V/V in the total reagent volume.

8. The kit according to claim 1, wherein the second volume further comprises at least one additional reagent selected from a deoxyribonuclease (DNAse) and a protease.

9. The kit according to claim 8, wherein the at least one additional reagent comprises DNAse.

10. The kit according to claim 8, wherein the at least one additional reagent comprises a protease.

11. The kit according to claim 10, wherein the protease comprises proteinase K.

12. The kit according to claim 1, wherein the disposable vessel is thermostable above 85° C.

* * * * *